United States Patent
Elkins

(10) Patent No.: US 6,695,872 B2
(45) Date of Patent: Feb. 24, 2004

(54) THERAPY COMPONENT OF AN ANIMATE BODY HEAT EXCHANGER AND METHOD OF MANUFACTURING SUCH COMPONENT

(75) Inventor: William Elkins, Santa Clara County, CA (US)

(73) Assignee: CoolSystems, Inc., Berkeley, CA (US)

( * ) Notice: Subject to any disclaimer, the term of this patent is extended or adjusted under 35 U.S.C. 154(b) by 248 days.

(21) Appl. No.: 09/765,082

(22) Filed: Jan. 16, 2001

(65) Prior Publication Data

US 2002/0138033 A1 Sep. 26, 2002

Related U.S. Application Data

(63) Continuation-in-part of application No. 09/493,746, filed on Jan. 28, 2000, now Pat. No. 6,178,562.

(51) Int. Cl.⁷ .................................................. A61F 7/00
(52) U.S. Cl. ........................ 607/104; 607/107; 607/108
(58) Field of Search ..................... 602/13; 607/104–112; 156/205; 5/706, 710

(56) References Cited

U.S. PATENT DOCUMENTS

| | | | | |
|---|---|---|---|---|
| 2,703,770 A | * | 3/1955 | Melzer | ........................ 5/710 |
| 3,561,435 A | * | 2/1971 | Nicholson | .................... 602/14 |
| 3,871,381 A | | 3/1975 | Roslonski | |
| 4,338,944 A | * | 7/1982 | Arkans | ........................ 607/104 |
| 5,022,109 A | * | 6/1991 | Pekar | ............................ 5/706 |
| 5,086,771 A | | 2/1992 | Molloy | |
| 5,172,689 A | | 12/1992 | Wright | |
| 5,230,335 A | | 7/1993 | Johnson, Jr. et al. | |
| 5,314,455 A | | 5/1994 | Johnson, Jr. et al. | |
| 5,411,541 A | | 5/1995 | Bell et al. | |
| 5,449,379 A | * | 9/1995 | Hadtke | ........................ 607/107 |
| 5,466,250 A | | 11/1995 | Johnson, Jr. et al. | |
| 5,989,285 A | | 11/1999 | DeVilbiss et al. | |
| 6,030,412 A | * | 2/2000 | Klatz et al. | .................. 607/104 |
| 6,352,550 B1 | * | 3/2002 | Gildersleeve et al. | ........ 607/108 |
| 6,371,976 B1 | * | 4/2002 | Vrzalik et al. | .............. 607/104 |

FOREIGN PATENT DOCUMENTS

| | | |
|---|---|---|
| WO | 9944552 | 9/1999 |
| WO | 0067685 | 11/2000 |

\* cited by examiner

*Primary Examiner*—Roy D. Gibson

(57) ABSTRACT

An embodiment of the present invention is a therapy component of an animate body heat exchanger that includes: (a) a bladder that contains a heat exchange medium, which bladder is compliant and is shaped to conform to a body part to be subjected to heat exchange; (b) a gas pressure bladder that overlays at least a portion of the bladder to direct gas pressure against the body part and against the portion to press the portion towards the body part, which gas pressure bladder is defined at least partially by a first pair of generally parallel walls; and (c) a plurality of first connections that connect the walls together interiorly of the gas pressure bladder to inhibit separation of the walls.

16 Claims, 5 Drawing Sheets

US 6,695,872 B2

THERAPY COMPONENT OF AN ANIMATE BODY HEAT EXCHANGER AND METHOD OF MANUFACTURING SUCH COMPONENT

CROSS REFERENCE TO RELATED APPLICATIONS

This application is a continuation-in-part of application Ser. No. 09/493,746 filed Jan. 28, 2000 U.S. Pat. No. 6,178,562 for CAP AND VEST GARMENT COMPONENTS OF AN ANIMATE BODY HEAT EXCHANGER, naming the applicant herein as the inventor.

BACKGROUND OF THE INVENTION

The present invention relates to animate body heat exchanging and, more particularly, both to a therapy component that includes a gas pressure bladder having a structure which inhibits unwanted expansion of the same, and a method of manufacturing such therapy component.

It is now common to apply cold and compression to a traumatized area of a human body to facilitate healing and prevent unwanted consequences of the trauma. In fact, the acronym RICE (Rest, Ice, Compression and Elevation) is now used by many.

Cold packing with ice bags or the like traditionally has been used to provide deep core cooling of a body part. Elastic wraps are often applied to provide compression.

It will be appreciated that these traditional techniques are quite uncontrollable. For example, the temperature of an ice pack will, of course, change when the ice melts, and it has been shown that the application of elastic wraps and, consequently, the pressure provided by the same, varies considerably even when the wrappers are experienced individuals.

Because of these and other difficulties, many in the field have turned to more complicated animate body heat exchanger. Most effective animate body heat exchangers typically include two major components, an external compliant therapy component covering a body part to be subjected to heat exchange, and a control component for producing a flowing heat exchange liquid. Many control units also produce and supply an air or other gas pressure needed to apply pressure to a body part and to press the heat exchange liquid toward such body part. This air pressure is directed to another compliant bladder of the therapy component, which air pressure bladder overlays the liquid bladder to press such liquid bladder against the body part to be subjected to heat exchange, as well as apply compression to the body part to reduce edema.

As can be seen, a commonly used external therapy component uses a pair of compliant bladders to contain fluids; that is, it preferably has both a compliant bladder for containing a circulating heat exchange liquid and a gas pressure bladder which overlays the liquid bladder for inhibiting edema and for pressing the liquid bladder against the body part to be subjected to heat exchange. One problem is that in many therapy component configurations of tis nature, the gas pressure bladder tends to "balloon" or, in other words, expand to a much greater degree than is desired. This unwanted expansion can be the cause of several problems. For one, it can actually pull away from the body part, some or all of the conformal heat exchange bladder. For another, it can reduce its edema inhibition ability, as well as reduce the desired effect of pressing the heat exchange bladder into contact with the body part.

SUMMARY OF THE INVENTION

The present invention is directed to remedying the above problems. From the broad standpoint it includes in a two bladder therapy component, a plurality of connections interiorly of the gas pressure bladder connecting such bladder's generally parallel walls together. In a preferred arrangement in which the bladders are formed together by heat sealing, a portion of the connections provided in the heat exchange liquid bladder to control and direct its flow are also provided in the gas pressure bladder, thereby providing the wall connections. In this connection, the preferred therapy component of the invention is made from three sheets of material. Two of such sheets are used to form a pair of walls for the heat exchange liquid bladder. The other sheet forms the outer wall of the gas bladder and cooperates with one of the other sheets to form the closed gas bladder. In other words, three sheets of material form two pair of walls defining the two pairs of bladders with one common wall.

The method of the invention relates to manufacturing the therapy component. In the preferred arrangement it is directed to heat sealing the various walls and connections to assure that connections are provided within the gas pressure bladder.

Other features and advantages of the invention either will become apparent or will be described in connection with the following, more detailed description of a preferred embodiment of the invention and variations.

BRIEF DESCRIPTION OF THE DRAWING

With reference to the accompanying sheets of drawing.

DETAILED DESCRIPTION OF THE PREFERRED EMBODIMENTS

Figure 1:
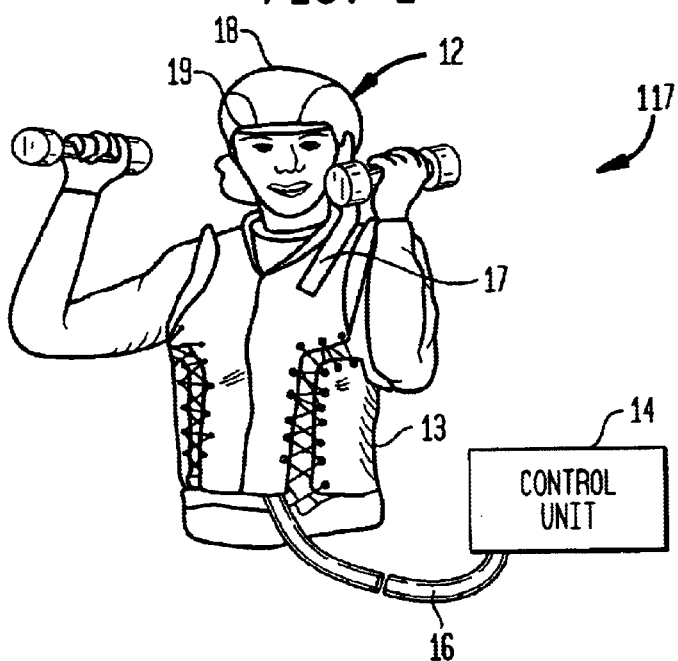
FIG. 1 is an overall isometric and partially schematic view of a preferred embodiment of the invention.

The following, relatively detailed description is provided to satisfy the patent statutes. It will be appreciated by those skilled in the art, though, that various changes and modifications can be made without departing from the invention.

A preferred embodiment of the animate body heat exchanger of the invention is generally referred to by the reference numeral 11 in the drawings. It includes a cap therapy component 12 serially connected with a vest therapy component 13. A control unit for the animate body heat exchanger is schematically represented at 14. Such control unit communicates with the therapy components via three tubes as will be discussed, extending through a tubular covering 16. The cap and vest therapy components 12 and 13, respectively, are connected in series with the control unit. That is, the vest therapy component is directly connected with the control unit as illustrated, whereas the cap component is connected to the vest through three tubes extending through covering 17. (In some situations, one control unit can be used to provide liquid circulation and gas pressure for two therapy components directly (in parallel) by, for example, having a connector on the unit for two therapy components. The control unit for a parallel therapy component arrangement can be quite similar to the one described.)

The purpose of the animate body heat exchanger of the preferred embodiment is to cool the head and torso of a human body. Thus, the control unit includes a mechanism for cooling and circulating a liquid coolant. In a practical realization of this preferred embodiment, the liquid was a 20 percent propylene glycol solution in distilled water with a small amount of a wetting agent to break surface tension, and an anti-fungicide such as iodine. This liquid was cooled by the control unit to between 45° F. and 50° F. by being passed through a heat exchanger in the control unit. In this connection, the control unit included an ice bath surrounding a container through which the liquid was circulated after being returned from the vest therapy component 13 and before it was reintroduced into such vest component. The control unit was capable of supplying liquid at other controlled temperatures and the pressure of air furnished by the control unit was generally about 0.25 psig.

It should be noted that the invention is applicable to many other types of therapy components, and the particular liquid, its temperature and pressure will be dependent upon the design and purpose of such therapy components. This is also true of the air pressure and in some instances it is cycled between two pressures (typically between 1.5 and 0.25 psig).

The cap therapy component 12 includes an outer covering 18 and a bill 19. Besides providing the visual appearance of a cap, the cover acts to cover or, in other words, hide the operational layers of she invention. The cover 18 also most desirably includes insulation, such as a layer of "Thinsulite™" to isolate the operational layers from the ambient atmosphere.

Figure 4:
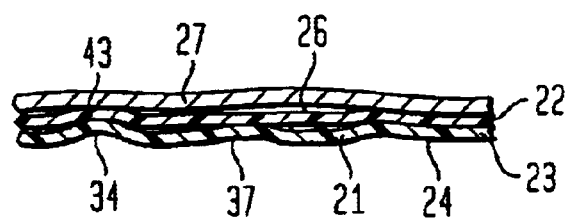
FIG. 4 is a partial sectional view showing the walls forming the head therapy component of the FIG. 1 preferred embodiment.

As best illustrated in the partial sectional view of FIG. 4, the operational layers include a compliant bladder 21 for containing the circulating heat exchange liquid. This bladder is defined by a pair of generally parallel and liquid tight flexible, or in other words, compliant walls 22 and 23, which walls are sealed together by, for example, heat sealing as indicated at 24. The invention also includes a compliant gas pressure bladder 26 which overlays the heat exchange bladder as illustrated to direct gas (most simply, air) pressure against a body part to inhibit edema and against the heat exchange bladder to press it towards the head. This compliant gas pressure bladder is also defined by a pair of generally parallel and flexible walls 22 and 27. In this connection, wall 22 is a common wall, i.e., one side of the same aids in defining the gas pressure bladder whereas the other side aids in defining the liquid bladder. Thus three compliant walls are all that is necessary to define the two separate bladders. (Wall 27 is also secured at 24 via heat sealing with walls 22 and 23.) Each of the walls 22, 23 and 27 is made of a nylon material suitably coated with a polypropylene to provide both the heat sealing qualities and the needed liquid or air impermeability.

As mentioned previously, one of the problems with therapy components of this nature is that the pressure bladder in certain circumstances tends to "balloon" under the air pressure. This is combated in the instant invention by providing a plurality of connections between the walls defining the air bladder. In this preferred embodiment in which the bladders are formed by heat sealing this is simply achieved by forming some of the connections normally provided in the liquid bladder while the sheet 27 is in place. The result is that these connections are also formed in the air bladder, that is, these connections are both within the liquid bladder and in the air bladder. It appears functionally as if the desired connections provided in the liquid bladder are "telegraphed" also to appear in the air bladder. These connections in the two bladders, of course, register with one another.

The details of this preferred embodiment are best understood if the heat exchange bladder 30 of the cap therapy component is first described.

Figure 2:
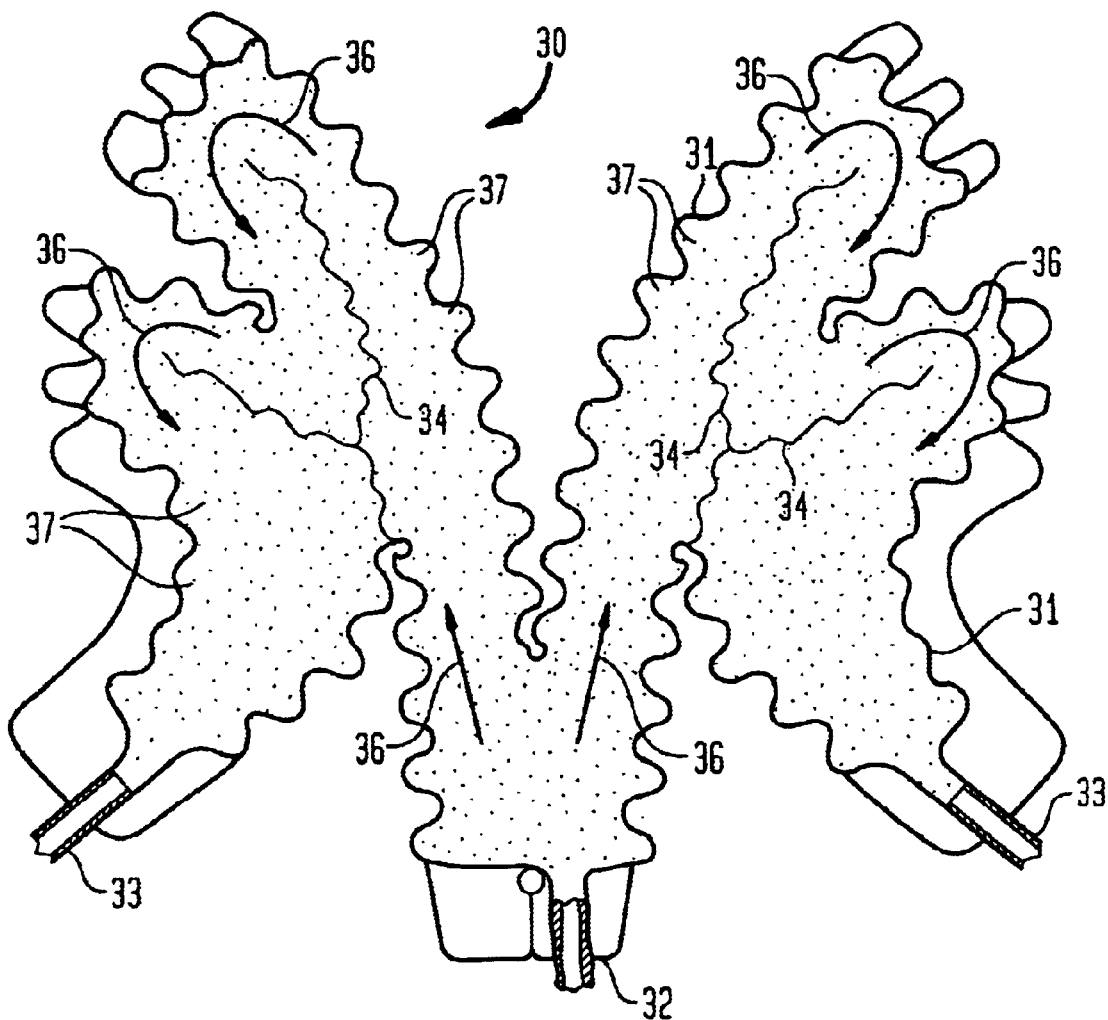
FIG. 2 is an elevation view of the interior of a heat exchange liquid bladder of a head therapy component, conforming to the preferred embodiment of the instant invention.

FIG. 2 shows the interior of such heat exchange liquid bladder. All major parts of this interior is defined by the surrounding curvilinear border represented at 31. Liquid is introduced into the central lobe of the same through a tube represented at 32. Such liquid flows to the ends of the side lobes having exit tubes 33. Its flow is directed by the border and a plurality of fences or, in other words, dividers which connect the walls together. This flow is indicated in FIG. 4 by arrows 36.

The connections in the interior of heat exchange liquid bladder 30 also include a relatively uniform distribution of dot connections 37. This matrix of connections acts to disperse the liquid throughout the bladder. Bladder 30 has a relatively complex shape to enable the same to conform to a head. This relatively complex shape is described in detail in application Ser. No. 09/493,746 filed by the instant inventor, and the disclosure of which is incorporated herein by reference. Suffice it to say, that among other points brought out in this earlier patent application the curvilinear border is such that the various adjacent sides of the lobes intermesh with one another.

Figure 3:
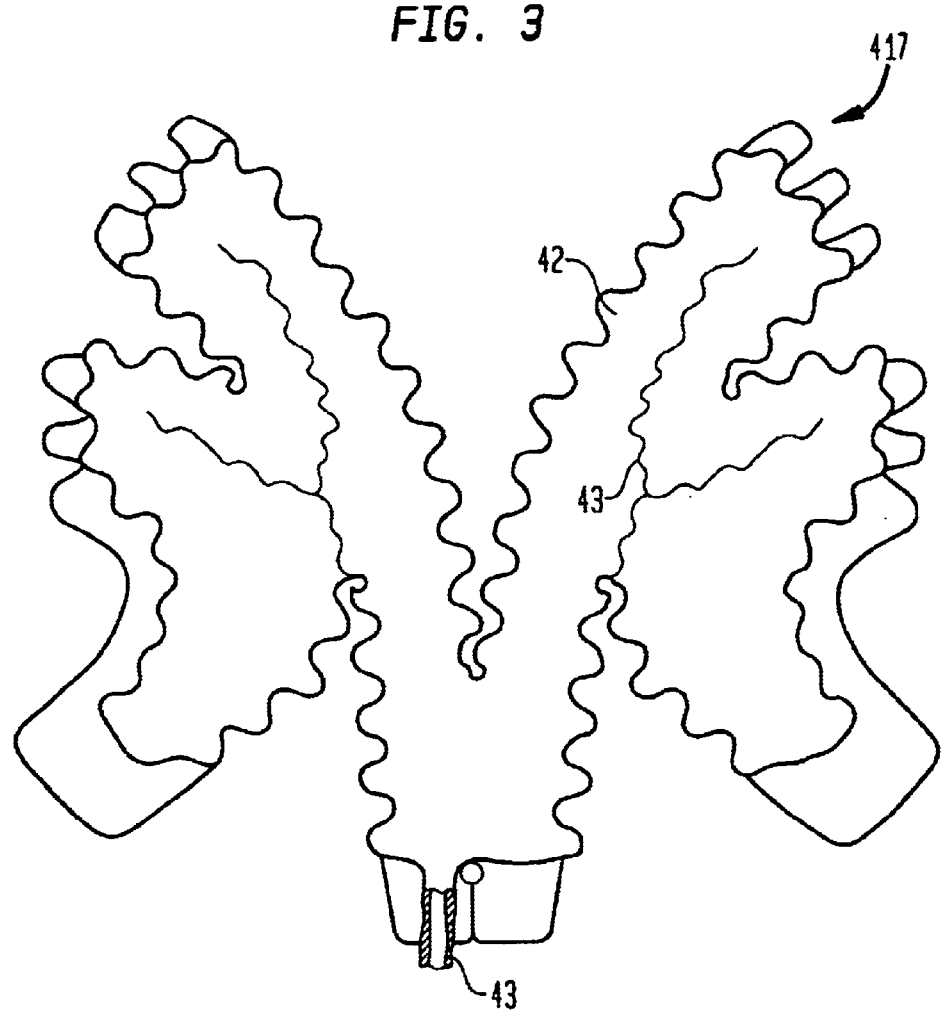
FIG. 3 is the interior of a gas pressure bladder of the head component of FIG. 1.

The heat exchange liquid bladder 30 is overlaid by a gas pressure bladder 41 shown in some detail in FIG. 3. The border for the operational aspects of the bladder is represented at 42, and air pressure is introduced into the bladder through tube 43. As illustrated, the shape of this gas pressure bladder conforms to the shape of the heat exchange liquid bladder 30. As a particularly salient feature of the invention, the fences or dividers in the liquid bladder are also provided in the gas pressure bladder. These fences are indicated by the reference numeral 43. They are provided in bladder 41 not for the purpose of directing the flow of a liquid or gas but to secure the walls defining the gas pressure bladder together at various locations within the interior of such bladder. These connections provided by the fences 43 will prevent the gas bladder from "ballooning" out and causing the temperature control liquid bladder not to conform to the body part. These fences register with the comparable fences in the liquid bladder.

During the manufacturing process, sheets of material defining the walls 22 and 23 are heat sealed together at the dot connections and if desired, at the interior fences. At a later time the wall 26 is heat sealed to the other walls with the interior fences being formed. Such fences 34 and 43 will thereby be formed in both bladders providing the desired liquid flows directors in the liquid bladder and the connections in the air bladder. This heat sealing will also form a common border for walls 22, 23, and 27. The resulting construction is represented in FIG. 3 which shows not only the dot connections 37 but also registering fence connections 34 and 43.

Figure 5:
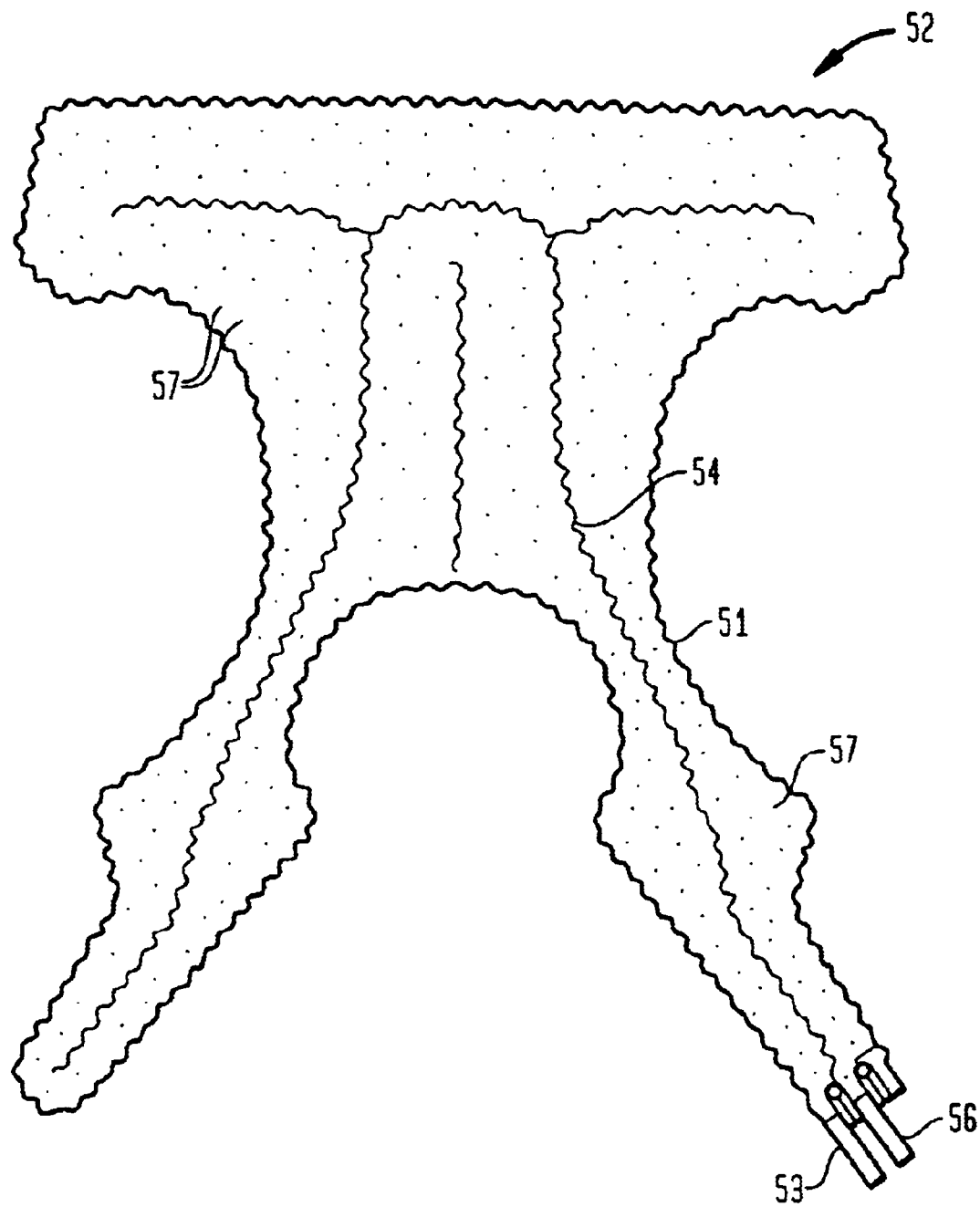
FIG. 5 is an elevation view of the interior of the heat exchange liquid bladder of a vest therapy component of the preferred embodiment.
Figure 6:
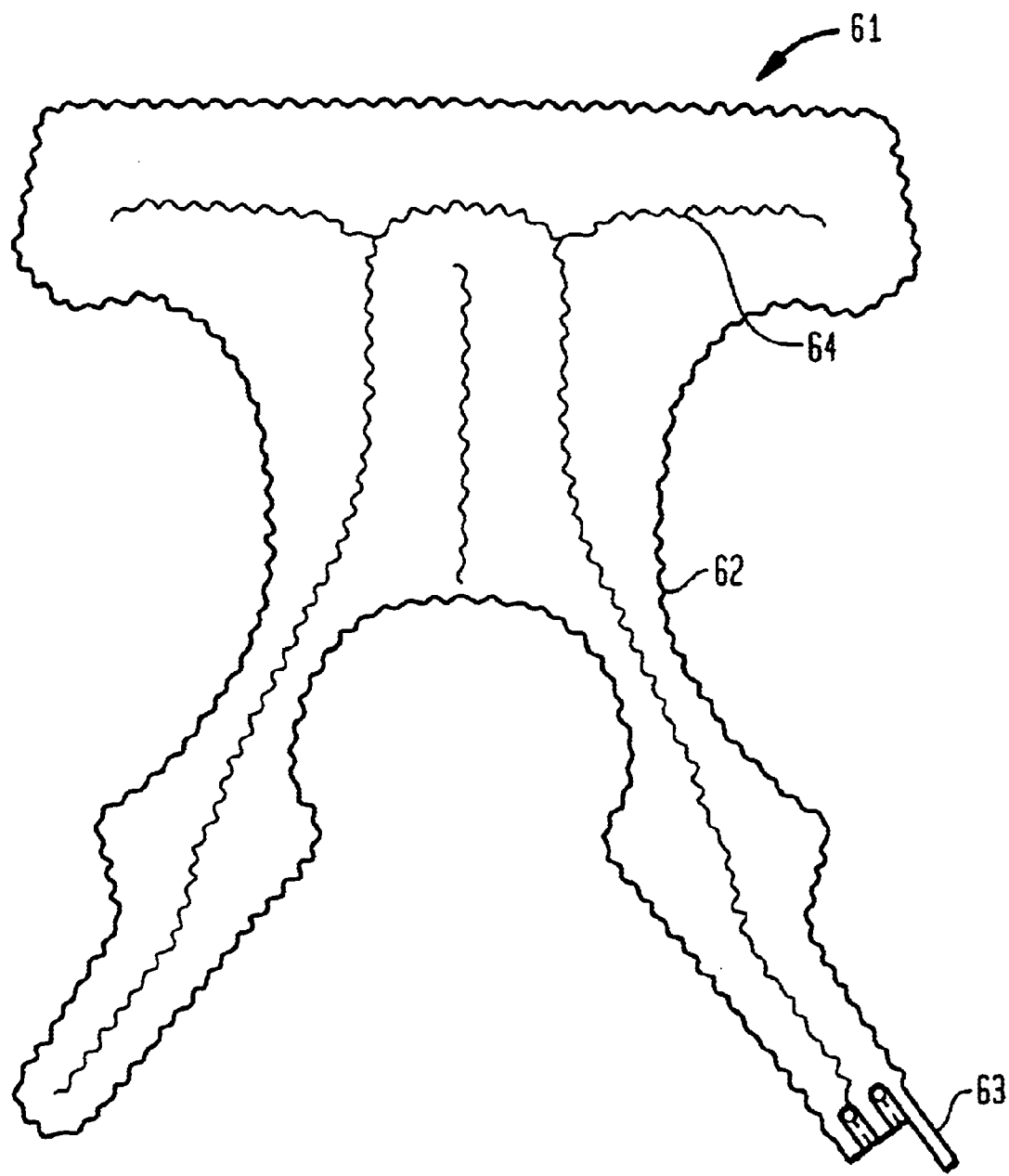
FIG. 6 is an elevation view showing the interior of the gas pressure bladder of the vest component

FIGS. 5 and 6 show an arrangement for the bladders of the vest garment therapy component similar to that of the cap component. With reference to FIG. 5, the border 51 of the heat exchange bladder 52 is defined by curvilinear ripples. Liquid is introduced into the bladder via inlet tube 53, flows throughout the bladder along a path defined by fences 54, and exits through exit tube 56. A matrix of dot connections 57 is provided throughout the interior to disperse the liquid and assure that all aspects of the torso are subjected to the heat exchange liquid.

The interior of the gas pressure bladder 61 is represented in FIG. 6. The border 62 is defined by curvilinear ripples which register with those of the liquid bladder, and air pressure is introduced into the same via tube 63. Such gas pressure bladder includes a fence configuration 64 which acts as the connections within the bladder between the walls. This fence configuration registers with the fence configuration in the liquid bladder shown in FIG. 5, with both this configuration and the fences in FIG. 5 being simultaneously formed by heat sealing in accordance with the manufacturing process discussed above for the cap therapy component. In this connection, the sheets of material from which the two bladders of the vest component are formed are heat sealable coated nylon. It is to be noted that in this arrangement, the dot connections are not also provided in the air pressure bladder.

Figure 7:
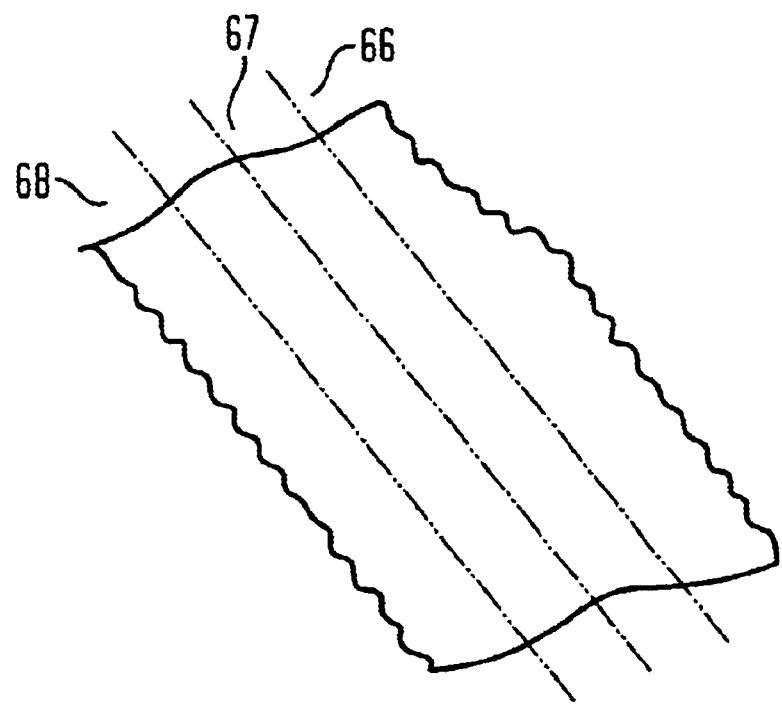
FIG. 7 is an enlarged partial isometric view showing one arrangement of connections in a gas pressure bladder.
Figure 8:
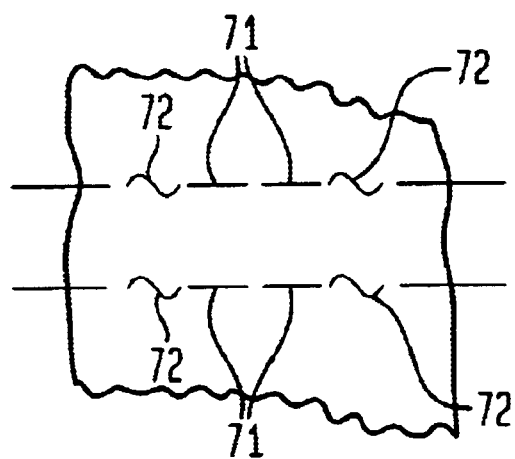
FIG. 8 is an enlarged partial elevation view showing another arrangement of connections in a gas pressure bladder.

It is contemplated that a selection of the dot connections can be made to provide a desired connection arrangement for an gas pressure bladder. Moreover, in some situations it may be desirable to use both dots and a portion of the fences in a liquid bladder to provide connections in the overlaying gas pressure bladder. FIGS. 7 and 8 are included simply to show such arrangements. In FIG. 7, a pattern of dots is selected to provide three linear connection locations represented by phantom lines 66, 67 and 68. (It does not have to be an orderly or otherwise recognizable pattern.)

FIG. 8 shows an arrangement in which both dots 71 and portions of fences 72 are selected to form a desired pattern. This type of combination is particularly useful when it is desired that the pattern of connections in the air pressure bladder register with connections in the liquid bladder that extend across flow "channels."

It should be noted that although straight line connections are shown, it is not necessary from the broad standpoint. The connections could form curvilinear lines or of any desired recognizable or unrecognizable pattern. Moreover, dots and all or parts of selected fences can be chosen to provide any desired pattern of connections. Again the pattern need not be recognizable.

As mentioned at the beginning of the detailed description, applicant is not limited to the specific embodiment and variations described above. They are exemplary, rather than exhaustive. For an example, it should be noted that the invention is applicable to many different therapy components as long as they have gas pressure bladders—the cap and vest garment arrangements of the preferred embodiment are utilized in this patent application to explain the invention. The claims, their equivalents and their equivalent language define the scope of protection.

What is claimed is:

1. A therapy component of an animate body heat exchanger, comprising, in combination:
   a bladder for containing a heat exchange medium, which bladder is compliant and is shaped to conform to a body part to be subjected to heat exchange;
   a gas pressure bladder overlaying at least a portion of the heat exchange medium bladder to direct gas pressure against said body part and against said portion to press the portion towards said body part, which gas pressure bladder is defined at least partially by a first pair of generally parallel walls;
   a plurality of first connections connecting said walls together interiorly of said gas pressure bladder to inhibit the separation of said walls; and
   a plurality of second connections interiorly of said heat exchange medium bladder to aid in directing a desired flow of said heat exchange fluid through the same.

2. The therapy component of claim 1 in which said bladder for containing a heat exchange medium is defined at least partially by a second pair of generally parallel walls.

3. The therapy component of claim 2 in which said bladders include a common wall which is both one of said first pair of walls and one of said second pair of walls.

4. The therapy component of claim 1 wherein said heat exchange fluid is a liquid.

5. The therapy component of claim 1 for an animate body heat exchanger wherein said first connections register with said second connections.

6. The therapy component of claim 1 for an animate body heat exchanger wherein said second connections are a dot matrix of connections for dispersing the flow of liquid in said heat exchange medium bladder.

7. The therapy component of claim 1 wherein said second connections are fences which direct the flow of liquid.

8. The therapy component of claim 7 for an animate body heat exchanger wherein said first connections register with said second connections.

9. The therapy component of claim 1 for an animate body heat exchanger in which said second connections are both fences for directing the flow of a liquid through said bladder and a matrix of dot connections for dispersing the flow of liquid around such bladder.

10. A therapy component of an animate body heat exchanger comprising, in combination:
    A. a bladder configured to direct the flow of a heat exchange liquid therethrough, which bladder is compliant and is shaped to conform to a body part to be subjected to heat exchange;
    B. a gas pressure bladder overlaying the heat exchange liquid bladder to direct gas pressure against said body part and against said heat exchange liquid bladder to press the same toward said body part, which gas pressure bladder is defined by a first pair of generally parallel walls and said heat exchange liquid bladder is defined by a second pair of generally parallel walls;
    C. a plurality of first connections connecting said first pair of walls together interiorly of said gas pressure bladder to inhibit the separation of said walls; and
    D. a plurality of second connections interiorly of said heat exchange liquid bladder to aid in directing desired flow of said heat exchange liquid through the same.

11. The therapy component of claim 10 in which said bladders include a common wall which is both one of said first pair of walls and one of said second pair of walls.

12. The therapy component of claim 10 for an animate body heat exchanger wherein said first connections register with said second connections.

13. In a method of manufacturing a therapy component of an animate body heat exchanger, the combination of steps comprising:
    A. securing a pair of generally liquid tight and compliant walls together to form a bladder for containing a heat exchange medium, which bladder is shaped to conform to a body part to be subjected to heat exchange;

B. securing a pair of compliant walls together to form a gas pressure bladder to overlap at least a portion of the heat exchange medium bladder; and C. forming a plurality of first connections between said pair of walls which form said gas pressure bladder, interiorly of said gas pressure bladder to inhibit the separation of said walls.

14. The method of claim 13 for manufacturing a therapy component of an animate body heat exchanger wherein said steps of securing the first and second pairs of walls together include heat sealing the same together simultaneously.

15. The method of claim 13 for manufacturing a therapy component of an animate body heat exchanger wherein said steps of securing said walls together to form said bladders includes heat sealing three sheets of material together to form both of said bladders with a common wall therebetween that is one of both of said pairs of walls.

16. The method of claim 13 for manufacturing a therapy component of an animate body heat exchanger wherein said step of forming a plurality of first connections includes heat sealing said pair of walls forming said gas pressure bladder, at a plurality of locations generally interiorly of said gas pressure bladder to form said connections.

* * * * *